United States Patent [19]

Pollack et al.

[11] Patent Number: 4,575,491

[45] Date of Patent: Mar. 11, 1986

[54] METHOD OF CONTROLLING AND DETERMINING GERMICIDAL ACTIVITY

[75] Inventors: William Pollack, Weston, Conn.; Oliver Iny, Little Neck, N.Y.

[73] Assignee: Euroceltique, S.A., Luxembourg

[21] Appl. No.: 615,835

[22] Filed: May 31, 1984

[51] Int. Cl.$^4$ ............................................. G01N 33/00
[52] U.S. Cl. ...................................... 436/125; 424/80; 436/178
[58] Field of Search ............... 436/124, 125, 126, 178; 424/80

[56] References Cited

U.S. PATENT DOCUMENTS 3,028,300  4/1962  Cantor et al. ........................ 424/80
4,320,114  3/1982  Denzinger et al. .................... 424/80

OTHER PUBLICATIONS

Prutton et al., "Fundamental Principles of Physical Chemistry", The Macmillan Co., New York, 1951, pp. 376–383.

Daniels et al., "Physical Chemistry–Third Edition", John Wiley & Sons, New York, 1966, pp. 173–176.

Primary Examiner—Arnold Turk
Attorney, Agent, or Firm—Steinberg & Raskin

[57] ABSTRACT

Iodine-containing germicidal preparations are provided with assured control of the content of equilibrium iodine in aqueous solution to be between 1 and 20 ppm, preferably 2–15 ppm so as to provide predetermined germicidal activity. The invention further comprises the determination of the content of equilibrium iodine in an aqueous iodophor solution by subjecting such solution to several extractions with different amounts of a water immiscible solvent for iodine, determining the concentrations of the equilibrium iodine in each of the amounts of the water immiscible solvent and extrapolating the concentrations to a theoretical zero value which is a measure of the equilibrium iodine in the aqueous iodophor solution. The invention further comprises improved germicidal iodophor compositions comprising an iodophor, citric acid and iodate.

8 Claims, 2 Drawing Figures

METHOD OF CONTROLLING AND DETERMINING GERMICIDAL ACTIVITY

BACKGROUND OF THE INVENTION

Iodine is a non-metallic element of the halogen family and is the only halogen that is solid at ordinary temperatures. Iodine has been shown to have a range in valance of from $-1$ to $+7$ and compounds thermodynamically stable with respect to their constituent elements are known to exist for all of the oxidation states of iodine.

Iodine was discovered early in the 19th century and the first practical therapeutic application of iodine was as a remedy for goiter. This use was followed shortly thereafter with the use as a germicide for the treatment of wounds. It was during the American war between the states that the first wide-spread use of iodine as an antiseptic and germicide was developed for the treatment of battle wounds. Since that time, iodine has been recognized to be a preferred germicide but because of certain inherent chemical, physical and biological properties, its antiseptic degerming use for humans and animals has been limited.

Elemental iodine has a high vapor pressure which results in pharmaceutical compositions having variable germicidal potency as the iodine content volatilizes from an antiseptic preparation on aging. Moreover the high vapor pressure of iodine contraindicates its use in closed compartments, such as body cavities or under a bandage because of corrosive destruction of skin, mucous membranes and other vital tissues. While the general systemic toxicity of iodine is low, fatalities have occurred after the ingestion of iodine solutions. However, the pathologic changes recorded for fatal cases of iodine poisoning are largely the result of tissue hypoxia and local corrosive destructive effects rather than systemic iodine poisoning.

Another limitation for the germicidal use of iodine is its high aqueous insolubility (0.034% at 25° C.). While the aqueous solubility of iodine may be increased through the use of alcohol (as for example, tincture of iodine) or through the use of inorganic metallic salts as solubilizing agents (as for example, sodium iodide and/or potassium iodide in the preparation of Lugols' Solution), such iodine solutions also possess the same toxic tissue manifestations which generally limit the use of iodine germicidal solutions.

When alcohol is used as a solvent for iodine, the use of such preparations on abraded and injured skin or mucous membranes is painful and damaging. Further, as the alcohol evaporates, the iodine content concentrates which increases the incidence of burning, corrosive destruction and staining of tissues.

Metallic iodides have been used to solubilize elemental iodine in water through the direct formation of a water-soluble iodine complex formed between the diatomic iodine ($I_2$) and the iodide ion ($I^-$) to form $I_3^-$ ions. Such aqueous iodine solutions have not modified the toxic tissue reactions of elemental iodine and burning and staining still occur. In fact, such untoward responses are now more frequent since larger concentrations of elemental iodine are utilized to prepare the aqueous iodine germicidal preparations.

Iodine in aqueous solution dissociates to equilibrate as follows:

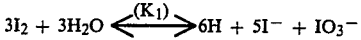

$$3I_2 + 3H_2O \underset{}{\overset{(K_1)}{\rightleftharpoons}} 6H^+ + 5I^- + IO_3^-$$

with the equilibrium constant ($K_1$) being about $4 \times 10^{-46}$ depending on the temperature. In aqueous media, the dissociation phenomena for diatomic iodine is further complicated by the formation of several species of iodide ion, the most significant of which is the tri-iodide ion. The equilibrium constant ($K_2$) being approximately $7.5 \times 10^2$.

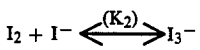

$$I_2 + I^- \underset{}{\overset{(K_2)}{\rightleftharpoons}} I_3^-$$

It is preferred to combine these equilibrium reactions when describing the dissociation of diatomic iodine in aqueous solutions as:

$$4I_2 + 3H_2O \underset{}{\overset{(K_3)}{\rightleftharpoons}} 6H^+ + 4I^- + I_3^- + IO_3^-$$

with the equilibrium constant ($K_3$) being approximately $3 \times 10^{-43}$.

Iodine is a mild oxidizing agent in acid solution with a redox equilibrium potential of 0.534 V at 25° C. for the iodine-iodide ion couple. Iodine will readily oxidize sulfite to sulfate and thiosulfate to tetrathionate, while ferric and cupric salts are reduced in acid solution by the iodide ion to form free iodine. In dilute solutions, iodine completely oxidizes sulfur dioxide to sulfuric acid, whereas iodides reduce sulfuric acid to sulfur dioxide, sulfur and even hydrogen sulfide, with the liberation of free iodine.

In neutral or slightly alkaline aqueous solutions, iodine exerts a somewhat stronger oxidizing action because of the formation of hypo-iodite ion in accord with the following reaction:

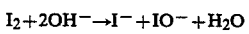

$$I_2 + 2OH^- \rightarrow I^- + IO^- + H_2O$$

Such aqueous solutions are strong iodinating agents and cause redox changes in body proteins and other biologic substances within the alkaline physiologic pH range. Iodine will add to unsaturated linkages in tissue proteins to cause denaturation which interrupt essential physiologic reactions.

In an effort to overcome the noxious tissue toxicity observed for aqueous and hydroalcoholic solutions of iodine, while at the same time maintaining the germicidal activity of elemental iodine, water soluble organic complexes of iodine with organic polymers were prepared. The combination of elemental iodine and certain organic polymers, as for example, polyvinylpyrrolidone and detergent polymers, was shown to increase the aqueous solubility of elemental iodine and such polymer-iodine products were termed, iodophors.

The organic polymers used to form an iodophor comprise a broad range in molecular weight and chain length and may be either ionic or non-ionic in character as well as to possess either surfactant or non-surfactant properties. A loose bond forms between the iodine and organic polymer to form the complex and aqueous solutions of up to 30 percent by weight in iodine content may be prepared.

The general class of organic iodophor compounds comprise two distinct polymer groups; the first group consisting of only one member, polyvinylpyrrolidone, which is a non-detergent, non-ionic and non-surface active polymer, the second group comprises the broad variety of detergent-surface active polymers including non-ionic, anionic and cationic surface active polymers. Both polymer groups are complexed with elemental iodine to form the iodophor.

The general method for the preparation of an iodophor complex is to bring into intimate contact, elemental diatomic iodine with the selected polymer either in the dry or powder form or in the presence of a suitable solvent. Heat may be used to accelerate complex formation. Upon completion of the reaction, the iodophor complex of the respective polymeric carrier with iodine is obtained in certain reproducible proportions of one to the other.

The widespread use of iodophor germicidal preparations has now established that problem of iodine tissue irritation; tissue staining and destructive corrosivity have been essentially eliminated through iodophor complexing although the germicidal potency known for elemental iodine remained essentially unchanged.

Studies have demonstrated that the microbicidal potency of iodophor germicidal preparations is essentially the same as that known for aqueous and/or alcoholic solutions of elemental iodine despite the modified tissue toxicity of iodophors. The superiority of the iodophor germicidal preparations over the aqueous and/or alcoholic inorganic elemental iodine solutions was shown to reside essentially in decreased toxicity, reduced tissue irritation, a lowered iodine vapor pressure as well as in the non-staining of skin and natural fabrics.

As the advantage of a lower incidence of untoward noxious tissue responses was established for iodophor germicides, efforts were directed toward developing methods to measure the quantitative extent of complexing between the iodine and the organic polymer in order to formulate iodophor germicidal preparations with improved stability and reproducibility.

Iodophor preparations are described in terms of available or titratable iodine which is considered to be the iodine released from the complex to exert its germicidal action. However, such available iodine determinations do not either reflect the total iodine content of the iodophor or its germicidal potency.

Iodophor solutions are also categorized on the basis of the amount of iodine extracted into an immiscible organic solvent which is expressed as the distribution coefficient for the preparation. Such extracted iodine is defined as uncomplexed or free iodine and is interpreted to reflect iodophor integrity. The uncomplexed iodine is postulated to be the cause of toxic responses, unstable and malodorous preparations and the distribution coefficient became the general measure to predict stability of the preparation on storage as well as the occurrence of toxic tissue responses.

The determination of the distribution coefficient for an iodophor solution, in accord with the teachings of the prior art, involves extracting exactly 1 ml. of an iodophor solution, having previously determined the amount of available iodine, with 25 ml. of heptane in a stoppered glass container. The iodine content in the heptane layer is measured spectrophotometrically at 525 mu. and the distribution coefficient (DC) calculated from the formula:

$$(DC) = \frac{\text{mg } I_2 \text{ in aqueous phase}}{\text{mg } I_2 \text{ in Heptane}} \times \frac{\text{mls. Heptane}}{\text{mls. aqueous phase}}$$

The relationship between the distribution coefficient and the quantitative degree of complexing present in an iodophor germicidal preparation was made on an empirical basis from the detection of an iodine odor in certain iodophor solutions but not in others. Iodophor solutions having a strong iodine odor were found to have a distribution coefficient of about 100 when determined by the above method. The iodine odor of such iodophor solutions lessened as the distribution coefficient reflected unsatisfactory polymer-iodine complexing and thereby gave rise to the odor because such solutions were presumed to have a large amount of free uncomplexed iodine. However, when the distribution coefficient for an iodophor solution was determined to be greater than 200, no iodine odor was detected and therefore satisfactory iodine-polymer complexing was assumed to be present. It was taught that the quantitative level of iodine complexing present in an iodophor compound was directly related to the distribution coefficient but inversely related to the strength of iodine odor detected (see for example U.S. Pat. No. 3,028,300).

However, it has been found that this test for iodophor integrity, noxious responses and germicidal potency by imputing the distribution coefficient as a measure of the degree of iodine bonding or polymer-iodine complex formation is in error because it does not recognize the complicated dynamic iodine equilibria present in aqueous iodophor solutions which form multiple thermodynamically stable or metastable states of iodine that are independent of the degree of polymer complex formation.

The dynamic systems present in aqueous iodophor solutions constantly establish new equilibrium states as iodine is removed by immiscible solvent in the course of the test method. The failure of the distribution coefficient to be a measure of iodophor complexing is readily demonstrated by a comparison of the properties of iodophor solutions with different distribution coefficients utilizing the criteria set forth in the art to establish the presence of satisfactory bonding.

Iodophor solutions were prepared in accord with the monograph for povidone-iodine solution of the United States Parmacopeia, Twentieth Revision, and were found to have a wide range in distribution coefficient when determined by the method of the prior art. These solutions were studied for the relationship between the distribution coefficient, intensity of iodine odor and the occurrence of tissue irritation. As a further basis for comparison and control, the solutions were compared with the properties of Strong Aqueous Iodine Solution, U.S.P., also known as Lugols' Solution, which is an uncomplexed inorganic aqueous solution of iodine.

The presence or absence of an iodine odor was determined organoleptically and the degree of iodine odor when present was graded on a scale of from 1+ to 4+ using the uncomplexed Strong Aqueous Iodine Solution as a reference control standard.

The distribution coefficient was determined in accord with the prior art method described above by extracting 1 ml. of the previously titrated U.S.P. povidone-iodine solution with 25 mls. of water-saturated heptane in a stoppered glass container which is maintained at 25° C.±1°C. The heptane layer is sampled and the iodine content in this layer determined at 525 mu with a Beckman Model DU-7 Spectro-photometer. The iodine remaining in the aqueous sample layer was calculated by difference. The distribution coefficient (DC) was calculated from the equation:

$$DC = \frac{\text{mg I}_2 \text{ remaining in aqueous phase}}{\text{mg I}_2 \text{ heptane}} \times \frac{\text{mls. heptane}}{\text{ml. aqueous layer}}$$

The Strong Aqueous Iodine Solution serving as a control preparation was treated in identical manner as described above. The test results for the solutions studied are presented in Table I.

The respective test solutions were then studied in rabbits for topical skin irritation. Each of the test solutions was applied to the skin of the shaved back of a rabbit and covered with a gauze patch. The irritation potential of the test solution to rabbit skin was read after 24 hours of contact. The results are reported in Table I.

TABLE I

| USP Povidone-Iodine Test Solutions | Distribution Coefficient | Odor | Rabbit Skin Irritation |
|---|---|---|---|
| No. 1 | 123 | No odor | No irritation |
| No. 2 | 44 | ++odor | No irritation |
| No. 3 | 35 | +++odor | Irritating |
| No. 4 | 338 | No odor | No irritation |
| No. 5 | 23 | No odor | No irritation |
| CONTROL PREPARATION | | | |
| Strong Aqueous Iodine Solution, USP | 18 | ++++odor | Irritating |

A comparison of the test results obtained for the respective solutions readily demonstrate that the distribution coefficient does not correlate with the criteria claimed in the prior art. The control solution, Strong Aqueous Iodine Solution, USP, which is an uncomplexed, inorganic aqueous solution, without an organic polymer, has a distribution coefficient of 18; a 4+ iodine odor and caused marked irritation to rabbit skin. Povidone-Iodine test solution No. 4 which had a distribution coefficient of 338 was without iodine odor and without skin irritation. The properties for these solutions are consistent with prior art criteria.

However, when the distribution coefficient determined for other iodophor preparations in the test series were compared with the prior art criteria, we find that the predictive value attributed to the distribution coefficient by the prior art to be inconsistent, variable and essentially meaningless to practice.

Povidone-Iodine test solution No. 5 which has about the same distribution coefficient as the uncomplexed control inorganic iodine solution, the Strong Aqueous Iodine Solution, (i.e., 23 vs. 18) has no iodine odor and does not cause skin irritation. Povidone-Iodine test solution No. 2 has a distribution coefficient of 44 but a 2+ iodine odor also does not cause skin irritation.

Contrasting properties are presented by povidone-iodine solution No. 3 which has a distribution coefficient to 35 and a 3+ iodine odor and is irritating. Povidone-Iodine Solution No. 1 which has a distribution coefficient of 123 which is markedly below 150, is without odor and is non-irritating.

These contrasting and unrelated differences in the response of iodophor solutions, when correlated with the distribution coefficient, demonstrate not only the unreliable meaning imputed to the distribution coefficient as a measure of iodophor integrity but also point to the inherent variability observed for the iodine distribution coefficient determined for iodophor solutions. Such variations in the iodine distribution coefficient for iodophor solutions are well known in the art. This variability in the distribution coefficient for an iodophor solution arise because the same molecular species is not present in both liquid phases.

The distribution coefficient for a solute is defined as the ratio in the amount of solute dissolved in two immiscible liquids at equilibrium. Since the distribution law (Nernst Law) is intended to express the behavior of only a single chemical species as it distributes itself between the two immiscible liquid phases, any tendency for the solute to be abnormally distributed in either phase results in a divergence from the normal distribution coefficient.

The iodine moiety of povidone-iodine complex is present in an aqueous iodophor solution in the form of different thermodynamically stable anionic iodine species and diatomic iodine. The anionic iodone forms are capable of generating diatomic iodine in the course of their respective equilibrium reactions. The anionic species do not distribute themselves into the extracting solvent which removes only the nonionic iodine. Such iodine is generated in the course of the iodine equilibrium reaction and its extraction by the solvent fractionates the equilibrium state. The disturbed equilibrium reaction is soon re-established to restore new anionic iodine species but now at a different concentration level since the previous aqueous iodine content of the solution has been reduced by the extracting solvent.

It is for this reason that the distribution coefficient for iodophor solutions will vary appreciably in practice because these values are determined upon the erroneous presumption that a single molecular species of the solute is present in each phase. The distribution coefficient which is intended to reflect the total concentration of the single solute in each phase is therefore meaningless as a measure of polymer complexing, iodophor integrity and as a predictive means for the occurrence of noxious skin irritations.

Since the iodophor iodine exerting the microbicidal action exists in solution in dynamic equilibrium with ionic iodine species, the removal of one or more of the iodine species results in the formation of new equilibrium forms. The extracting solvent removes or consumes iodine from the iodophor solution in a manner similar to that of the microbial and organic load during the degerming use of the iodophor solution. The amount of iodine available for germicidal action in an iodophor preparation therefore, is the amount of iodine in the equilibrium in the solution at the time of its use. Such equilibrium iodine content represents the germicidal potency of the preparation but not the total iodine content titrated for the preparation nor the apparent distribution of iodine determined for two solvents as taught in the art. Although iodophor solutions are assayed in the art for available or titratable iodine, it is the equilibrium iodine which is the particular form of iodine present in the iodophor solution that is instantly available to exert the microbicidal action. This form of iodine differs from titratable iodine and the other iodine species present in the iodophor solution and the equilibrium iodine content of an iodophor solution is to be distinguished from its titratable iodine content.

The titratable iodine content of an iodophor preparation includes the iodine reservoir of the iodophor preparation povidine iodine to the particular dynamic equilibrium reactions occurring in an iodophor solution as well as the equilibrium iodine in the solution.

Titratable Iodine = Reservoir Iodine + Equilibrium Iodine However, it is the equilibrium iodine alone that exerts the microbicidal action of the preparation at any given moment. The portion of the titratable iodine content remaining after subtracting the amount of equilibrium iodine present serves as the iodine reservoir to generate new equilibrium iodine in solution as it is consumed by the microbial and bio-organic load in the course of microbicidal activity but does not exert such germicidal action by itself.

It is thus necessary to devise a simple method for determining the content of equilibrium iodine in an iodine solution, and thus to have a measure of the germicidal activity of such solution.

SUMMARY OF THE INVENTION

Accordingly, it is an object of the present invention to provide a method of measuring the equilibrium content of an iodophor solution.

It is another object of the present invention to provide for the control of the content of equilibrium iodine in an iodophor solution to thereby provide for control of the germicidal activity of such solution.

It is yet a further object of the present invention to provide improved germicidal solutions containing specific quantities of equilibrium iodine.

It is yet another object of the present invention to provide improved germicidal solutions containing iodine, citric acid and iodate.

With the above and other objects in view, the present invention mainly comprises the determination of the content of equilibrium iodine in an aqueous iodophor solution which contains iodine bound to the iodophor and iodine in solution, the bound and solution iodine being in equilibrium with each other, by subjecting a predetermined quantity of the aqueous iodophor solution to several extractions with different amounts of a water immiscible solvent for the iodine, determining the concentrations of the equilibrium iodine thus extracted into each of the amounts of the water immiscible solvent, and extrapolating the concentrations of equilibrium iodine to a theoretical zero value of the solvent, the extrapolated value being a measure of the equilibrium iodine in the iodophor solution, the same constituting the amount of iodine available for germicidal action.

In carrying out this method, several aliquots of the iodophor solution are extracted with varying quantities of a water-immiscible solvent, followed by determination of the iodine concentration in the different amounts of water-immiscible solvent used for the extraction. An equation of relationship is then analyzed from these data, to determine iodine concentration in the differing amounts of water-immiscible solvent, as a function of the actual amount of solvent used for the extraction.

A graph of this relationship is then prepared, with the plot of the relationship extrapolated to a theoretical "0" value (i.e. the Y-intercept on the line), which is used as a measure of the iodine available for extraction in the iodophor solution itself.

More specifically, the present invention is directed to extracting an iodophor solution with several ratios of water-immiscible solvent:iodophor solution, relatively small ratios in the range of 1:1, 2:1, 3:1 and relatively high ratios in the range of 50:1 100:1 and 150:1 of water-immiscible solvent:iodophor solution. Each of these different extraction ratio ranges that is, the low and high range is then analyzed to determine two separate relationships between the amount of iodine extracted by the two ranges of water-immiscible solvent, as a function of the volume ratio and of two equilibrium constants $K_1$ and $K_2$ namely according to the formulas:

$$Y_1 = A_1 e^{-K_1 V} \text{ and } Y_2 = A_2 e^{-K_2 V}$$

Y = mass of $I^0_2$ extracted
V = volume ratio water-immiscible solvent:iodophor solution
k = equilibrium constant
A = constant at 0-volume ratio.

Two such individual extraction equations are determined, and can be individually analyzed and plotted on a graph. From the two equations $Y_1$ and $Y_2$ are calculated to determine the RPF, namely the iodine content of the iodophor solution that can be rapidly released for a quick germicidal effect, and the overall MPF, the total amount of $I^0_2$ that is available for degerming. The MPF-RPF is a measure of the reservoir effect contained within the iodophor solution.

$$\text{The RPF} = A_1 V_x e^{-k_1 V_x}$$

Where $V_x$ is the volume ratio where the two curves intersect, that is:

$$V_x = \frac{\log e \frac{A_1}{A_2}}{K_1 - K_2}$$

In a like manner:

$$MPF = \frac{0.3679 A_2}{K_2}$$

The method of the present invention now makes it possible to completely analyze the iodine content within an iodophor solution, not only in terms of equilibrium iodine, namely the $I^0_2$ available for quick degerming effect, but also the total available iodine that can be utilized for ultimate germicidal action, including the equilibrium iodine, iodide ions present in solution, plus reservoir iodine present within the PVP complex. Once these amounts of the various types of iodine are analyzed, the iodophor solution may then be adjusted in terms of pH, and the changing equilibrium constant k, to provide greater or less amount of equilibrium iodide available for germicidal action, as desired. This is a distinct advantage in the preparation and utilization of such iodophor solutions, because it is now possible to control the overall germicidal action based on analysis of the iodophor solution in terms of extractions thereof by water-immiscible solvent.

BRIEF DESCRIPTION OF THE DRAWINGS

The present invention will be described in further detail with reference to the enclosed drawings, in which.

DETAILED DESCRIPTION OF THE PREFERRED EMBODIMENTS

Figure 1:
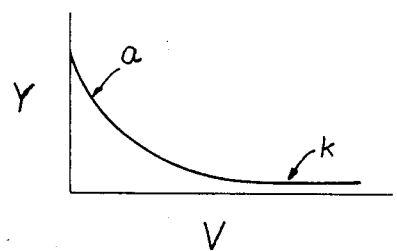
FIG. 1 is a graph of a relationship between iodine extracted from an iodophor solution by varying amounts of water-immiscible solvent in single, fairly close proportions.

The present invention will be described with reference to preferred embodiments thereof, which are merely intended as exemplary, and are not intended to limit the scope of the present invention in any way.

Any suitable iodophor solution may be analyzed by the method according to the present invention. For example, such iodophor solutions may be prepared in accordance with the monograph for povidone-iodine solution of the United States Pharmacopeia, 20th Revision. Any other conventional additives to such an iodophor solution may be included.

The iodine content itself measured in the iodophor solution, may be of several different types. For example, iodine in an iodophor solution may tend to dissociate by any one of the following four equations:

$$3I_2 + 3H_2O \quad 6H + 5I^- + IO_3^-$$

$$I_2 + I^- \quad I_3^{--}$$

$$4I_2 + 3H_2O \quad 6H^+ + 4I^- + I_3^- + IO_3^-$$

$$I_2 + 2OH^- \quad I^- + IO^- + H_2O$$

The iodine content of an iodophor solution is really a measure of several different types of iodine present in such a solution. For example, the equilibrium iodine, $I^0{}_2$, in solution, is a measure of the quick-kill germicidal activity readily available in an iodophor preparation. This equilibrium iodine content is determined as described above by extraction with a water-immiscible solvent, such as heptane.

The "total iodine" in an iodophor solution, includes not only this equilibrium iodine, but also the "reservoir iodine", iodine which, though not immediately available for germicidal effect, may nevertheless be converted to equilibrium iodine for antimicrobial action. Such reservoir iodine includes the various iodide ions, such as $I_3^-$, in solution, plus all PVP-trapped iodine. As equilibrium iodine is extracted out of solution, some of this reservoir iodine is also converted to equilibrium iodine, $I^0{}_2$. thus it is termed "reservoir iodine", because it provides a readily-available reservoir to replenish extracted-out equilibrium iodine.

The "titratable" iodine, is naturally a measure of the iodine present in an iodophor solution that is available for titration. This includes the $I^0{}_2$, along with such free iodine $I^0{}_2$ as part of the tri-iodide complex $I_3^-$. This tri-iodide complex is really a combination of $I^- + I_2$, hence there is free iodine that is available for titration as part of this tri-iodide complex, which does not necessarily constitute a part of the equilibrium iodine. This total "titratable" iodine is also termed free iodine, including the equilibrium iodine, and the free iodine part of the tri-iodide complex.

Another important measure in analyzing an iodophor solution, are the distribution or equilibrium constants $k_1$ and $k_2$. This is a measure of the ratio of the equilibrium iodine:total iodine in an iodophor solution. When extracting with a water-immiscible solvent, this is also a measure of the concentration of iodine in the extracted solvent amount:the iodine remaining in the aqueous iodophor solution. Concentration is measured in terms of mg/ml. This equilibrium or distribution constant k changes over the range of extractions carried out with a water-immiscible solvent, and is also dependent on the pH of the iodophor solution itself.

In the method of the present invention, a predetermined amount of an iodophor solution is extracted with specific differing amounts of a water-immiscible solvent such as heptane. Other suitable water-immiscible solvents include benzene, ethyl ether and cyclohexane. The extraction ratios of immiscible solvent:iodophor solution are relatively low, in the range of about 1:1 to about 5:1. For example three such extractions in ratios of 1:1, 3:1 and 5:1 are carried out. Then, the concentrations of iodine in each of the amounts of water-immiscible solvent used for the extraction, is determined.

The extraction may be carried out by shaking a mixture of immiscible solvent and the iodophor solution followed by centrifuging, in a conventional centrifuge. Then, the iodine absorbed into the water-immiscible layer is spectrophotometrically measured and the value plotted as a function of the volume of water-immiscible solvent used for the extraction. In a preferred embodiment, the natural logarithm (log e) of the value is plotted against the volume ratio of water-immiscible solvent:volume of iodophor solution used in each extraction. A "least-square-fit" line is drawn through the points representing the water-immiscible solvent iodine absorbence, with the line extrapolated to the point of zero-solvent volume ratio, i.e. the "Y-intercept" line in the graph (see FIG. 1).

This extrapolated zero-volume absorbed value determined from the graph, is then compared with a reference standard iodine solvent solution, prepared by dissolving a predetermined amount of iodine into the same water-saturated solvent. The absorbence of this reference standard solution is then spectrophotometrically determined as noted above, with the ultimate amount of iodine available for extraction at the zero-volume solvent ratio being calculated from the following equation:

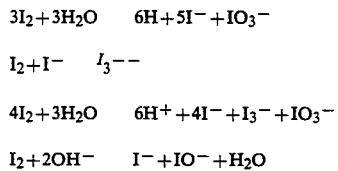

$$\text{mg } I_2 \text{ ml ref. std.} = \genfrac{}{}{0pt}{}{\text{(Iodine concentration available for)}}{\text{(extraction at 0-volume solvent ratio)}}$$

The value obtained is then converted into the amount (mg/ml) of Equilibrium Iodine in the iodophor solution by dividing the iodine concentration available for extraction at the zero-volume ratio by the distribution constant (K) determined for iodine for the particular solvent system used in accord with the following formula:

$$\frac{\text{Iodophor mg } I_2 \text{ at 0-Volume Ratio}}{(K) \text{ determined for Solvent System}} =$$

Mg/ml Equilibrium Iodine in the Iodophor Solution to provide the amount of (mg/ml) of equilibrium iodine present in the iodophor preparation to exert its microbicidal action. The concentration of equilibrium iodine is a measure of the microbicidal potential of the iodophor solution and is independent of the amount of titratable iodine determined for the particular solution.

It was found that iodophor solutions containing different amounts of available iodine and different amounts of equilibrium iodine exert a killing action directly related to the amount of equilibrium iodine present but not to the available iodine content for the same solution. An iodophor solution with the greater equilibrium iodine content will exert superior microbicidal action to an iodophor solution having greater titratable iodine content but a lesser amount of equilibrium iodine.

The total from this equation will equal the amount of iodine concentration available for extraction in the iodophor solution at zero volume solvent:iodophor solution ratio. This iodine concentration available for extraction is a measure of the ultimate equilibrium iodine present in the iodophor solution. This value must then be converted into the amount (mg/ml) of equilibrium iodine in the iodophor solution, by dividing the iodine concentration available for extraction at the zero-volume ratio by the distribution constant k determined for iodine for the particular solvent system.

From the plot illustrated in FIG. 1, the slope k of this line is determined at the Y-intercept. Accordingly by dividing the iodine concentration at the zero-volume ratio by the value of the Y-intercept, the ultimate amount of equilibrium iodine present in the iodophor solution can be determined.

The graph illustrated in FIG. 1 fits the equation $Y_1 = A_1 e^{-K_1 V}$, where these individual symbols indicate the definitions noted above. Thus the value of $A_1$ is a measure of the ultimate value of the equilibrium iodine available for extraction, when divided by k (A/k).

The same procedure can be carried out with extractions of water-immiscible solvent:iodophor solution of greater ratios, such as on the order of 50:1 to about 150:1. Mixture in a centrifuge is carried out in a similar fashion, along with ultimate spectrophotometric analysis. In this situation, a different curvilinear plot is determined as a function of the volume ratio.

Figure 2:
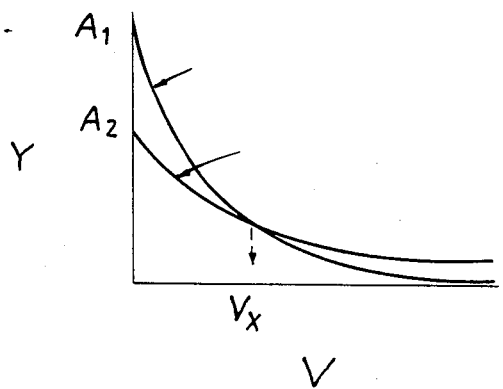
FIG. 2 is a graph of two separate extractions of the iodophor solution with varying amounts of water-immiscible solvent, each of the separate extractions being carried out by greatly differing amounts or ratios of immiscible solvent:iodophor solution, to provide the two distinct separate plots as illustrated.

An estimate of the RPF and MPF is determined from the data of repeated extractions, to solve for the constant $A_2$ and $K_2$ in the second equation $Y_2 = A_2 e^{-k_2 v}$, for this second group of extractions. As clearly illustrated in FIG. 2, the graphs of these two different lines for the two different areas of extraction, meet at a certain volume $V_x$. Both the plots are curvilinear in nature, with the initial plot becoming asymptotic to the V axis and with the second plot becoming asymptotic to the V axis.

These two separate curves are then used to determine the RPF and MPF. More specifically, the volume element $V_x$ represents the intersection point of the two equations for $Y_1$ and $Y_2$. The mass of iodine that can be extracted by this volume is a convenient measure of the more easily removed or less tightly bound iodine. It is determined simply as the concentration extracted by volume $V_x$ and multiplied by this volume. That is:

$$\text{Mass of } I_2 \text{ extracted} = A_1 V_x e^{-K_1 V_x}$$

$$\text{Where, } V_x = \frac{\text{Log } e \frac{A_1}{A_2}}{K_1 - K_2}$$

We have called this the "relative potency factor" (R.P.F.) In a similar way the total mass of iodine that can be extracted is given by, $$\text{"Maximum Potency Factor"} = A_2 V_m e^{-K_2 V_m} = \text{M.P.F.}$$

Where $V_m$ is the volume of the solvent that extracts the most iodine. This equation describes a parabolic curve, the maximum of which is:

$$\frac{d(V_m Y_2)}{d(V_m)} = 0$$

i.e. $A_2 K_2 V_m e^{-K_2 V_m} = 0$

Expanding by the binomial theorum but ignoring all terms past the second, $$A_2 K_2 V_m - A_2 K_2^2 V_m^2 = 0$$

and $$V_m = 1/K_2$$

Substituting:

$$MPF = \frac{A_2 e^{-1}}{K_2} = \frac{0.3679 A_2}{K_2}$$

Thus the method of the present invention will provide an accurate measure of not only the RPF, namely the iodine immediately available for a quick germicidal effect, but also of the total iodine present in the reservoir and available in the iodophor solution, MPF, for ultimate total germicidal activity. This also takes into account the changing nature of the equilibrium constant, k, with respect to the two individual curvilinear graphs that are plotted. As is easily seen, this equilibrium constant changes by the amount of water-immiscible solvent used for extraction, and is also greatly dependent upon the nature of the pH of the iodophor solution used in the extraction. Thus, based on the determination of these graphs, the equilibrium constants $K_1$ and $K_2$ can be adjusted, by adjusting the pH of the iodophor solution, to provide a more desirable level of equilibrium iodine, either greater or lesser, that is immediately available for a germicidal kill effect (RPF). It should be pointed out that the successive extractions may be carried out with either increasing or decreasing amounts of water-immiscible solvent; the exact progression of such extractions is not critical so long as differing amounts of water-immiscible solvents are used.

Tests were carried out to determine the roll of equilibrium iodine to microbicidal activity.

Two aqueous solutions of povidone-iodine (USP) were prepared so that the first solution contained 330 mgm/100 ml. titratable or available iodine and 9.2 ppm. equilibrium iodine and the second solution contained 440 mgm/100 ml. titratable iodine and 0.9 ppm. equilibrium iodine. Both solutions were adjusted to the same pH. The microbicidal action against B. pumulus spores for both solutions was determined in side-by-side testing by measuring the time required to cause a three (3) log reduction in the number of B. pumulus spores treated with the respective solution. The three (3) log decrease in the number of organisms from the base line number is recognized by the U.S. Food and Drug Administration to be effective degerming for an iodophor preparation and this value was adopted as the objective measure of microbicidal action for this test. The results are reported in Table 2.

It was found that the first solution (solution A) which had the smaller quantity of titratable iodine but the greater quantity of equilibrium iodine achieved the three-log reduction of B. pumulus spores in less than three hours, whereas the second solution (solution B) having the larger amount of titratable iodine but the smaller amount of equilibrium iodine required more than seven and a half hours to achieve the same three (3) log reduction of the base line number of spores.

TABLE 2

The Relationship Of Titratable Iodine And Equilibrium Iodine To Killing Time (*B. pumulus* spores)

| Test Solution | Titratable* Iodine | Equilibrium** Iodine | 3-Log Killing Time *B-pumulus* Spores |
|---|---|---|---|
| Solution A | 330 mg/100 ml | 9.2 ppm. | less than 3 hours |
| Solution B | 470 mg/100 ml | 0.9 ppm. | more than 7.5 hours |

*Determined by the method of the U.S. Pharmacopeia for Providone-Iodine Solution

**Determined by the method described above.

This study clearly demonstrates the critical role of equilibrium iodine to microbicidal potency for an iodophor solution. The function of remaining iodine portion of the amount of titratable iodine determined in the iodophor solution, apart from the equilibrium iodine is as a reservoir iodine resource to replace equilibrium iodine as it is consumed by the microbial and bio-organic load. This constant generation of equilibrium iodine from the reservoir iodine resource in the iodophor solution permits ongoing germicidal action in the presence of varying bio-organic and microbial loads.

It is important to establish the preferred range of concentration for equilibrium iodine to obtain optimal germicidal activity. Although in theory as long as equilibrium iodine is present, microbes will be destroyed. However, in the dynamics of the biologic system, the rate of microbial destruction must be greater than its regeneration. The microbicidal action of any substance depends upon multiple factors including:

a. The inherent resistance of the organism to microbicides b. The number of organisms present c. Specific microbicidal potency of the germicide, and d. Regenerative power of the organism.

It is known that iodine interacts with certain physiologic organic compounds, proteins, carbohydrates and reducing substances such as sulfhydryl groups present in blood, pus and other biologic fluids. These substances present in living cellular materials consume iodine to deplete both the equilibrium iodine and the reservoir iodine of the iodophor solution as it is used in degerming practice.

It was unexpectedly found that minimal quantities of the iodate ion act to attenuate the resistance of microbial flora to iodine to result in a synergism whereby materially smaller quantities of equilibrium iodine are required for effective germicidal action. The iodate ion is without germicidal properties. However, when organisms are exposed to the iodate ion, an attenuation of their inherent biologic resistance is observed.

In a study to evaluate the effect of the iodate compound in attenuating the inherent resistance of microorganisms to germicides, microorganisms were exposed to the iodate compound at the physiologic pH range. At this pH range the oxidizing potential of the iodate compound is virtually eliminated. After exposure the organisms were washed free of any iodate compound and it was found that the killing time for iodine was materially reduced.

It was further found that when the iodate compound is mixed directly with povidone-iodine and when microorganisms are exposed at a physiologic range, that a synergistic effect is observed so that the iodophor microbicidal activity is enhanced about 50%. Thus, resistant organisms which require 30 seconds exposure to povidone-iodine for effective degerming were now killed in less than 25 seconds when mixed with the iodate compound and the povidone-iodine solution.

A preferred ratio of iodine to iodate compound is 0.5 parts iodine and 0.25 parts of iodate compound although it was found that a ratio as low as one part iodine to one part iodate compound would be effective for certain organisms.

When an iodophor solution is used to treat a heavily contaminated wound, the generation of equilibrium iodine must occur at a faster velocity than when the same solution is used to treat a relatively clean wound. So long as the reservoir iodine is sufficient to maintain equilibrium iodine levels, the microbicidal action of the iodophor preparation will remain constant (See FIG. 2). The germicidal activity terminates when there is no longer any reservoir iodine available to generate new equilibrium iodine as it is consumed in the course of degerming action. Since the removal of equilibrium iodine by the microbial flora and bio-organic load is counteracted by the reservoir iodine resource as the depleted equilibrium iodine is regenerated, the capacity to generate equilibrium iodine becomes critical to both the duration of germicidal activity and the microbicidal power of the preparation.

The resource iodine available to regenerate equilibrium iodine at any given moment comprises both the iodine in solution as anionic species together with the iodine held within the coiled polymer chains and in the interchain, non-polar aggregates of the povidone polymer strands. While the principal resource iodine reservoir comprises the anionic iodine species solution, as for example, $I_3^-$, $I_5^-$ and $I_7^-$, together with the other polar iodine containing moieties, other iodine reservoirs are present to contribute resource iodine to generate equilibrium iodine. These iodine reservoirs comprise the iodine bound into the three-dimensional non-polar spaces in the coiled polymer molecule. Such three-dimensional regions are formed as a result of random coiling of the polymer chain in water in such a way that the hydrophilic pyrrolidone groups face outwards to the water thus shielding the non-polar aliphatic $CH_2$—$CH_2$—CH backbone. In this manner, polyvinylpyrrolidone in water acts to incorporate the insoluble diatomic iodine into the hydrophobic non-polar regions so that iodine is distributed between the solvent water molecule and the hydrophobic portions in the helix of the coiled polymer, polyvinylpyrrolidone.

In addition to the iodine atoms held inside the helix of the coiled polymer in solution, it has been shown that interchain polymer aggregates form which retain both diatomic and polar iodine. The polymerization of the monomer, vinylpyrrolidone, results in the formation of a polymer with a broad range in chain length. In solution, the polyvinylpyrrolidone molecule consists of a flexible chain that is stretched to achieve maximal interaction with water. As the concentration of the polymer in solution changes or when solutes such as iodine are added to solutions of the polymer, new intramolecular and intermolecular linking reactions occur which effect both molecular shape of the polymer chain as well as influence the mobility of the iodine solute.

As the povidone-iodine solutions are diluted, the distances between polymer strands is increased. The compressed chains now expand so that maximal interaction with the polar solvent occurs. Polymer disaggregation results and releases stored reservoir iodine which increases the amount of iodine to enter into the equilibria of the solution. In this manner an increase in the solubility of diatomic iodine in water occurs since the povidone acts as a miscible solvent for the iodine when the iodophor is dissolved in water.

The principle iodine resource for the regeneration of equilibrium iodine however, is the predominant iodine species $I_3^-$, which exists both in the free state as well as being bound to the polar hydrophilic centers of the povidone polymer. While the exact structure of the povidone iodide complex has not as yet been fully elucidated, it has been shown that the polymer povidone will combine with about one mol of iodine for each mol of monomer and such combination involves an ionic bond. Although certain iodine anion, as for example $I_5^-$ and $I_7^-$ form by the selective complexing between elemental iodine and the appropriate precursor derivative iodine anion, the recovery of iodine from $I_3^-$ anion is the major iodine resource species to be considered for equilibrium iodine regeneration. These equilibria may be illustrated as follows:

Povidone $I_3^- \rightleftharpoons$ Povidone + $I_3^-$ $I_3^- \rightleftharpoons I_2 + I^-$ As equilibrium iodine is consumed, there is a proportionate increase in the amount of $I^-$ in solution which shifts the direction of the anionic equilibrium reactions thereby slowing the regeneration of equilibrium iodine. However, as the level of undissociated $I_3^-$ concentration increases, the non-ionic iodine held within the coiled chains as well as by the polymer aggregates enter into separate equilibrium reactions to counterbalance the increased $I^-$ concentration.

Povidone $I_2 \rightleftharpoons$ Povidone + $I_2$ $I_2 + I^- \rightleftharpoons I_3^-$ This new iodine resource reverses the direction of the respective anionic iodine equilibrium reactions to facilitate the generation of new equilibrium iodine maintaining germicidal activity. In this manner the reactions involving anionic iodine are responsible for the maintaining the immediate germicidal potency of the iodophor preparation while the availability of resource non-ionic iodine enables the persistence of germicidal activity by providing microbicidal capacity or substantivity to the iodophor preparation in response to the microbiologic demand.

Polyvinylpyrrolidone, or povidone, is the homopolymer of 1-ethylenyl-2-pyrrolidinone and is available over a wide range of molecular weight. Povidone is classified by K-values which are assigned to the povidone polymers to reflect their average molecular weight. These constants, i.e., K-values, are derived from viscosity measurements in accord with the well known Fikentscher's formula and the smaller the K-value, the lower the molecular weight and the intrinsic viscosity of the polymer.

Commercially available povidone polymers have K-values of K-15, K-30, K-60 and K-90, and in aqueous solutions, povidone K-15 and povidone K-30, which pertain to the lower portion of the molecular weight range of the polymer, have little effect on viscosity in concentrations below 10% whereas povidone K-60 and povidone K-90, with higher average molecular weights have considerable influence on the flow properties of a solution.

Povidone forms molecular adducts or complexes with many substances to result in a solubilizing action for certain materials as for example, iodine but also a precipitation effect for others as for example, polyacids and tanins. Cross-linking of the povidone polymer often accompanies complex formation and is influenced by many diverse factors as for example, actinic light, diazo compounds, oxidizing agents and heat. Certain substances in a povidone solution as well as pH will accelerate cross-linking of the polymer strands at even lower temperatures. When a povidone solution is heated to 100° C. in the alkaline pH range, the polymer becomes permanently altered to become irreversibly insoluble. Similar cross-linked changes occur when alkaline sodium phosphate buffers are used. When oxidizing agents are added to a povidone solution, cross-linking gel formation occurs in about 30 minutes when the combination is heated at moderate temperatures of about 90° C.

The cross-linking of the povidone polymer strands results in polymer aggregates which entrap solutes. The competition between intra and intermolecular cross-linking is an ongoing phenomena which is also influenced by the amount of ionizing substances in solution as well as the concentration of polymer. In dilute solutions, the mobility of the polymer chain and the average chain-to-chain distances between neighboring microradicals serve to minimize the level of intra-molecular cross-linking. Conversely, as the chain-to-chain distances between neighboring micro-molecules shorten cross linking increases. Branching of the macromolecular polymer chain prevents the large molecules from aligning themselves in close proximity to one another as well as to interfere with the orderly arrangement of the molecules and chain configuration. Irregularity of the coiled chain configuration results in the presence of large empty spaces which are filled with solvent and/or solute.

A study of the optical density of different concentrations of povidone-iodine solution demonstrate that the optical density is not linearly dependent from the concentration of iodophor to establish that the povidone-iodine complex is of varying structure. The variations in the structure of the povidone-iodine polymer chain is also reflected in that the stability of the iodophor in aqueous solution decreases as the concentration of the iodophor in solution decreases. This observation suggests that the formed complex between the polymer and iodine also includes polymer chain aggregates of the accommodating iodine as well as the tri-iodide ion.

The interaction of the polymer chain resulting in polymer aggregation also contributes to the binding of other ions in solution. The extent of polymer aggregation is a function of the total ionic strength of the solution as well as the variety of independent ionic species in solution. If the ionic strength of the particular iodine species in the solution is increased by a large margin, then ionic competition occurs to release the bound tri-iodide ion as well as to dissociate the polymer aggregate. The release of the bound tri-iodide ion results in an increased equilibrium iodine concentration as well as to reduce the viscosity of the iodophor in solution.

The release of tri-iodide ions is measured by enhanced light absorption of the solution with a shift of the absorption maxima. Studies of the interaction between tri-iodide ion and the polymer, polyvinylpyrrolidone, reveal the tri-iodide ion to be complexed in a rather close environment of the polymer as reflected in the variations of the optical density of the solution. Thus we find that not only is iodine bound to the polymer but also the tri-iodide anion is similarly complexed.

Inter-molecular polymer interaction usually involve hydrogen and coulombic bonds through the pyrrolidone rings which interact with a hydrogen ion located between the carbonyl oxygen. However, the pyrrolidone ring, per se, is unable to maintain the iodine complex in water and aqueous solutions of tri-iodide ions show no enhancement in light absorption in the presence of N-methyl pyrrolidone. Moreover, the solid complex of N-methyl pyrrolidone with iodine decomposes when dissolved in water.

When the polyvinylpyrrolidone molecule is in aqueous solution it is known to assume a flexible chain configuration in rather extended form in order to achieve maximal interaction with the aqueous polymer solvent. When iodine is added to a solution of polyvinylpyrrolidone, a time-dependent, non-conformational change in the polymer configuration and space occurs so that it becomes folded in order to achieve a more efficient interaction with iodine. However, as the amount of water, relative to the amount of polyvinylpyrrolidone in solution is reduced, as for example, when the polymer concentration increases or when iodine is removed from the solution, then the polymer configuration will change.

This change in the structure of polyvinylpyrrolidone-iodine complex in aqueous solution is demonstrated through optical density measurements of the solution and is known to be a function of the ratio of the amount of tri-iodide ion in solution relative to the concentration of polyvinylpyrrolidone polymer. The optical density of a polyvinylpyrrolidone-iodine aqueous solution containing a constant amount of tri-iodide ion ($I_3^-$) will increase as the concentration of polyvinylpyrrolidone increases.

The optical density of the tri-iodide in solution reflects the stability of this anion. Changes in optical density indicate the corresponding shift in the direction of its equilibrium dissociation reaction in the solvent. Therefore, as an increase in the concentration of polyvinylpyrrolidone relative to the volume of solvent water occurs, or as the amount of solvent water decreases in proportion to the amount of polyvinylpyrrolidone present in solution, these changes influence the amount of tri-iodide ion present in solution.

When diatomic iodine becomes more readily available as it dissociates from the polymer, it coordinates with the iodide anion to form the stable tri-iodide anionic form. The formed tri-iodide ion then enters into the solvent-anion equilibrium reactions to provide equilibrium iodine, the essential microbicidal iodine species in the iodophor solution. It is in this manner that the polyvinylpyrrolidone-iodine complex serves as the iodine resource to generate microbicidal equilibrium iodine on demand. As the iodine is utilized in the course of degerming, more of the polymer, polyvinylpyrrolidone, becomes available to increase the ratio of polyvinylpyrrolidone to solvent and thereby making available new equilibrium iodine from the dissociated resource iodine. In practice the application of the iodophor solution to the infected skin site facilitates the evaporation of the water solvent to increase the polyvinylpyrrolidone content which also provides resource iodine as degerming progresses.

Commercially available polyvinylpyrrolidone-iodine complex ranges in iodine content of from 9.0 percent to 12.0 percent by weight, when determined by titration and calculated on the dry basis. Therefore, the availability of resource iodine in the iodophor solution will vary among separate commercial batches because the different iodine content contributes to differing polymer-anion ratios and influences the degree of internal and interchain linkages formed.

It is known that dilute solutions of polyvinylpyrrolidone-iodine are less stable to aging than more concentrated iodophor solution. This finding is in agreement with the demonstration that the povidone polymer assumes a non-formal helical configuration and to form intermolecular linkages which cause an exclusion of water to achieve a more stabilized form. Since the degree of intermolecular interaction decreases upon dilution, more diatomic iodine is made available to generate the separate anionic iodine species in solution which then enter into equilibrium reactions with the solvent thereby depleting the available iodine reserve.

Although the expected result of dilution of an iodophor solution is a decrease in iodine content, we have unexpectedly found an increase in equilibrium iodine content for the same diluted iodophor solution. Dilution of the iodophor solution makes available more resource iodine to be converted into equilibrium iodine thereby increasing the overall microbicidal power of the solution. However, this finding only pertains to certain critical limits. Obviously ultimate dilution, wherein zero iodophor concentration is achieved, does not result in maximal increased equilibrium iodine content. Similarly, increasing the concentration of the iodophor in a solution to release resource iodine to generate general equilibrium iodine also has its practical limits. In the anhydrous state, the dry solid iodophor complex is without microbial killing power since no equilibrium iodine is generated in the absence of solvent water.

While the normal tendency for the polymer in solution is to form such intermolecular aggregates thereby holding the diatomic iodine in a more stable form, such aggregation restricts the utilization of all of the iodine available in the iodophor solution to generate equilibrium iodine.

It is known that certain agents such as poly acids, ammonium persulfate, alkaline sodium phosphates, as well as oxidizing agents, diazo compounds and heating will promote cross-linking of the polyvinylpyrrolidone polymer. It is important to recognize that such agents as alkaline phosphates and polyacids, as well as oxidizing substances are present in iodophor solutions and these may act to facilitate aggregation with consequent iodine entrapments.

It was found that when the ionic strength of the iodophor solution is not less than 0.1 g.i./L that the tendency for intermolecular aggregation is virtually eliminated and disaggregation of the polymer chain facilitated so that the full potential of the iodine content is made available to generate equilibrium iodine. Moreover, when the ionic strength is adjusted to be above the value set forth above disaggregation occurs irrespective of whether poly acids, alkaline sodium phosphates and even oxidizing substances such as iodate are present in the solution.

In practice the ionic strength of the solution may be determined by conductometric measurements and the ionic strength for the solution calculated. Such determination is readily carried out during the course of the manufacture of the solution and appropriate ionic volumes adjusted to achieve the optimal disaggregation protective ionic strength for the solution. Evidence of the facilitated stabilized disaggregation status of the polymer is reflected in the modified viscosity measurements for the polymer solution.

It was found that at least 1 ppm. of equilibrium iodine must be continuously present to achieve effective microbicidal action under clinical use conditions, wherein the microbial bio-organic load rapidly consumes the equilibrium iodine. Unless there is an adequate supply of resource iodine to regenerate equilibrium iodine, highly diluted iodophor solutions are essentially worthless for clinical germicidal use, despite an elevated equilibrium iodine content.

While the microbicidal power of an iodophor solution has been shown to be a function of the concentration of equilibrium iodine, the germicidal utility of the particular iodophor solution is dependent on the capacity of the particular preparation to regenerate the equilibrium iodine as it is consumed. The variation in the ratio of the amount of iodine to polyvinylpyrrolidone in the iodophor complex as is known for the commercially available iodophor raw materials, materially affects the availability of resource iodine to generate equilibrium iodine. Such variation thereby results in differing potencies and persistence of microbicidal activity often with disastrous consequences.

In the presence of a high bio-organic load, an iodophor solution requires a greater capacity to regenerate equilibrium iodine than is needed to degerm a relatively clean skin site. The capacity to regenerate equilibrium iodine together with the rate at which such resource iodine becomes available is critical to the overall performance of the germicide. At times an extremely rapid delivery of resource iodine would be required while at other times a slow, steady supply of resource iodine would be indicated to serve the individual needs.

An important consideration of the rate of availability of the resource iodine is the possibility of tissue trauma which may occur when huge amounts of germicidal iodine are brought into contact with abraded or traumatized skin. Thus control over the rate of release of resource iodine is essential to superior germicidal preparations. The capacity of an iodophor preparation to make available resource iodine to regenerate equilibrium iodine may be measured by determining the whole amount or mass of diatomic iodine which may be liberated to generate equilibrium iodine. Chemically, this is equivalent to the total mass of equilibrium iodine generated within the particular polyvinylpyrrolidone solution for microbicidal action.

The rate of utilization of the iodine resource iodine reserve is proportional to the rate at which the equilibrium iodine is consumed and this is proportional to the solute pressure or the total concentration of iodine available to generate equilibrium iodine in the preparation.

In the course of clinical degerming the regeneration of equilibrium iodine occurs at virtually the same rate as it is consumed and a convenient method for determining the capacity of the solution to deliver equilibrium iodine has not been hitherto available. While product performance tests over periods of time, as for example, the glove juice germicidal action test, has been used to measure microbicidal persistence or substantivity, the results of this test cannot be used as an index of overall or maximal germicidal potency. We have found a test model which permits the convenient determination of the capacity of an iodophor solution to generate equilibrium iodine in the presence of repeated utilization or decomposition of its equilibrium iodine content.

If it were possible to extract all of the equilibrium iodine generated in the solution into a sufficient volume of an immiscible solvent and then determine the amount of equilibrium iodine extracted in the solvent, a measure of the maximal potency of the preparation would be obtained. However, the technical manipulation of such a sufficiently large volume of an immiscible solvent is not feasible. An alternative means would be to utilize successive extractions with large volumes of the immiscible solvent until the equilibrium iodine content of the solution is exhausted. Since at each extraction point the amount of equilibrium iodine removed from the solution would be equivalent to its utilization, then this rate of utilization in terms of milligrams of the equilibrium iodine per unit time may be stated by the equation:

$$da/dt = kc$$

where k is the proportionality constant. Since "a" will have the same dimensions as "c", this equation may now be written as:

$$da/dt = ka$$

and when we integrate from zero time to a finite time:

$$\ln a/a_0 = -kt$$

and $$a = a_0 e^{-kt}$$

Since "a" is the liberated amount of equilibrium iodine at each extraction point and $a_0$ is the concentration able to be liberated, then $a_0$ is a measure of the maximal potency for the preparation. Therefore a plot of log a, that is, the solvent concentration of iodine at each extraction, versus time should be linear since:

$$\ln a = a_0 - kt$$

It is important to note that the proportionality constant "k" is the absorption equilibrium constant which also defines the ability of the iodophor solution to deliver resource iodine.

The measure of the maximal potency for an iodophor solution is conveniently determined by extracting a volume of the iodophor solution with a series of increasingly larger or smaller volumes of an immiscible solvent as for example, heptane. As the extraction solvent volume is increased or decreased, a progressively larger or smaller mass of iodine, respectively, will be removed when two successive different solvent volumes extract essentially the same amount of iodine, that is, an asymptotic plateau is reached and the extraction is stopped. The optimal density of the extracted iodine in the solvent is measured and the amount of iodine extracted by the particular solvent volume (Vi) is expressed by the equation:

$$Y_i = a(1 - me^{-kvi})$$

where m is the equilibriumiodine content in the iodophor solution at the time of extraction and m is expressed as a fraction of the total regeneration equilibrium iodine "a". This equation describes the fact that as iodine is extracted into the solvent from the iodophor solution, this concentration for any solvent volume (Vi) is:

$$(-me^{-kvi})$$

where m is the equilibrium iodine content of the solution and the mass of iodine remaining in solution is:

$$1 - me^{-kvi}.$$

Transforming the above equation, we obtain:

$$Y_i = a - ame^{-kvi}$$

which can be solved for "a" by iterative procedures. The asymptope "a" is the total resource or replaceable iodine at the temperature of the experiment, and is a measure of the maximum potency for the solution. The results obtained by the iterative procedure are identical to the value found by the simplified equations. Thus, the maximum potency factor is the amount of iodine that is available to regenerate equilibrium iodine as it is removed on the course of the microbicidal action of the preparation.

By determining the content of equilibrium iodine in the iodophor solutions, in accordance with the present invention, it then becomes possible to adjust the quantity of equilibrium iodine to achieve an effective germicidal action. In accordance with the present invention the amount of equilibrium iodine should be at least 1 ppm. In general, quantities greater than 20 ppm are not necessary. Accordingly, the preferred concentration for the present invention is between 2 and 15 ppm, most preferably between 4 and 10 ppm.

As indicated above, the germicidal action of the iodophor iodine is potentiated by iodate ions. In accordance with one embodiment of the invention, a wound site or the like, can first be treated with a solution of iodate ions and then with the iodophor solution. It is preferred, however, to incorporate iodate ions in the iodophor solution, preferably in a ratio of iodine to iodate of between 2:1 and 1:1.

In accordance with a further preferred embodiment of the present invention, citric acid is added to the iodophor-iodate solution. The amount of the citric acid is preferably between about 2–10 times the amount of the iodate compound.

The following examples are given to further illustrate the present invention. The scope of the invention is not, however, meant to be limited to the specific details of the examples.

EXAMPLE 1

50 g of povidone iodine, assayed as having 10% w/w available iodine, was dissolved in 500 ml of purified water. 20 ml of this prepared iodophor solution was pipeted into a screw cap centrifuge with an equal volume (20 ml) of water-saturated heptane being added, so that the ratio of heptane:iodophor solution is 1:1.

This resulting mixture was shaken for 5 minutes at 25° C., and then centrifuged for 2 minutes at 3,000 rpm. The absorbence of iodine into the upper heptane layer was then spectromically measured with a 1 cm cell in a Beckman DU-7 spectrophotometer, against water-saturated heptane at a maximum absorbence of 525 nm, and determined to be 0.196.

This extraction step was again repeated with the same amount of iodophor solution being pipeted into the screw cap centrifuge, but utilizing two volumes of heptane to one volume of the iodophor solution (2:1). The absorbence of the upper heptane layer was again spectrophotometrically measured after centrifugation, for iodine present in heptane solution, determined to be 0.180.

Extraction was again carried out as in the first two extraction steps, but with 60 ml of heptane so that the ratio of heptane to iodophor solution is 3:1. Centrifugation and absorbence analysis were again carried out, as in the first two extraction steps, with absorbence determined to be 0.176.

This heptane-iodine absorbence for each separate extraction step, as spectrophotometrically determined, was plotted against the volume ratio of heptane:iodophor solution in each particular extraction step. A "lease-square-fit" curvilinear line was drawn through the points representing the heptane-iodine absorbence, and the line was extrapolated to the point of zero-solvent volume ratio, i.e. the "Y-intercept" line on the graph.

The extrapolated zero-volume absorbence value was determined to be 0.205, this absorbence value when converted to $I_2$ concentration and divided by the partition coefficient (48) was 1.17 ppm this constituting the amount of equilibrium iodine.

0.1 g of potassium iodate, predissolved in 30 ml of purified water, is then added. A buffer solution is prepared by dissolving 6.60 g of citric acid and 19.20 g of sodium citrate in the 100 ml of purified water and the buffer solution is then added. The pH is adjusted to 4.8 with either citric acid or sodium citrate, as required. Then 0.5 g of potassium iodate is dissolved in 70 ml of purified water and this solution is added. The desired final volume of 1 liter is reached by the addition of purified water. The assay for equilibrium iodine is effected as above described and is found to be 3.3 ppm.

EXAMPLE 2

Example 1 is repeated, however utilizing 2 g of potassium iodate. The resulting assay for equilibrium iodine determines the value to be 4.8 ppm.

EXAMPLE 3

Example 1 is repeated, however, adjusting the pH to 4.8 and adding 4 g of potassium iodate to the solution. The equilibrium iodine value is found to be 8.5 ppm.

EXAMPLE 4

Example 1 is repeated, however with 45.5 g of povidone iodine assayed to 11% w/w available iodine. The final value of the equilibrium iodine determined after the addition of the potassium iodate is found to be 3.3 ppm.

EXAMPLE 5

Example 4 is repeated, however with the addition of 2 g of potassium iodate. The equilibrium iodine value is found to be 4.8 ppm.

EXAMPLE 6

Example 4 is repeated, however with the adjustment of the pH to a value of 4.8 and the addition of 4 g of potassium iodate. The final equilibrium iodine content is found to be 8.5 ppm.

EXAMPLE 7

Example 1 is repeated, however with 41.7 g of povidone iodine assayed to 12% w/w available iodine. The equilibrium iodine value determined after the addition of the potassium iodate is found to be 3.3 ppm.

EXAMPLE 8

Example 7 is repeated, however with the addition of 2 g of potassium iodate. The final value of the equilibrium iodine is found to be 4.8 ppm.

EXAMPLE 9

Example 7 is repeated, however adjusting the pH to a value of 4.8 and adding 4 g of potassium iodate. The final equilibrium iodine is found to be 8.5 ppm.

What is claimed is:

1. Method of determining the content of equilibrium iodine in an aqueous solution of an iodophor, said solution containing iodine bound to said iodophor and iodine in solution, the bound iodine and solution iodine being in equilibrium with each other, comprising the steps of:

subjecting a predetermined amount of said aqueous iodophor solution to several extractions, each with a different amount of a water-immiscible solvent for iodine, thus extracting equilibrium iodine into each of said amounts of said water-immiscible solvent, determining the concentrations of said equilibrium iodine in each of said amounts of said water-immiscible solvent, and extrapolating the thus determined concentrations of equilibrium iodine to a theoretical zero value of said water-immiscible solvent, the extrapolated zero value being the amount of equilibrium iodine in said aqueous iodophor solution, the same constituting the amount of iodine available for germicidal action.

2. Method according to claim 1, and further comprising the step of adjusting the amount of said equilibrium iodine in said iodophor solution to a predetermined amount, thereby obtaining a desired microbicidal activity.

3. Method according to claim 2, wherein the amount of equilibrium iodine is adjusted to a value of between 1-20 ppm.

4. Method according to claim 2, wherein the amount of equilibrium iodine is adjusted to a value of 2-15 ppm.

5. Method according to claim 2, wherein the amount of equilibrium iodine is adjusted to a value of 4-10 ppm.

6. Method according to claim 1, wherein said water-immiscible solvent is heptane.

7. Method according to claim 1, wherein said different amounts of water-immiscible solvent for iodine are progressively increasing amounts.

8. Method according to claim 1, wherein said different amounts of water-immiscible solvent for iodine are progressively decreasing amounts.

* * * * *